(12) United States Patent
Theis et al.

(10) Patent No.: US 6,242,599 B1
(45) Date of Patent: Jun. 5, 2001

(54) PROCESS FOR THE PREPARATION OF GUANINE

(75) Inventors: Christoph Theis, Niederkassel; Stephan Bruhn, Handorf, both of (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/384,215

(22) Filed: Aug. 27, 1999

(30) Foreign Application Priority Data

Aug. 27, 1998 (DE) .............................. 198 39 013

(51) Int. Cl.⁷ .................................. C07D 473/18
(52) U.S. Cl. ............................................. 544/276
(58) Field of Search ............................... 544/276

(56) References Cited

U.S. PATENT DOCUMENTS

| | | | |
|---|---|---|---|
| 4,701,526 | 10/1987 | Kobe et al. | 544/251 |
| 4,868,302 | 9/1989 | Schneider | 544/320 |
| 4,948,890 | 8/1990 | Schneider | 544/320 |
| 5,663,338 | 9/1997 | Ramert et al. | 544/277 |

FOREIGN PATENT DOCUMENTS

| | | |
|---|---|---|
| 41 36 114 | 5/1993 | (DE) . |
| 0 267 594 | 5/1988 | (EP) . |
| 0 415 028 | 3/1991 | (EP) . |

OTHER PUBLICATIONS

Wilhelm Traube, Chem. Ber., 33, 1900, 1371–79.*
J. H. Lister, "Purines", Wiley–Interscience, New ork, 1971, p 33–34.*
Roland K. Robins et al., "Purines. II. The Synthesis of Certain Purines and the Cyclization of Several Substituted 4,5–Diaminopyrimidines", Synthesis of Purines and Cyclization of 4,5–Diaminopyrimidines, Jan. 20, 1953, pp. 263–266.

* cited by examiner

*Primary Examiner*—Mark L. Berch
*Assistant Examiner*—Thomas Mcenzie
(74) *Attorney, Agent, or Firm*—Oblon, Spivak, McClelland, Maier & Neustadt, P.C.

(57) ABSTRACT

A process for the preparation of guanine, by reacting 2,4-diamino-5-formylamino-6-hydroxypyrimidine (DAFHP) with formic acid, in the absence of formalize. The process may be conducted with the addition of water and at reflux temperature.

18 Claims, No Drawings

PROCESS FOR THE PREPARATION OF GUANINE

BACKGROUND OF THE INVENTION

1. Field of the Invention

The present invention relates to a process for the preparation of guanine (2-amino-1,9-dihydropurin-6-one), starting from 2,4-diamino-5-formylamino-6-hydroxypyrimidine (DAFHP).

2. Discussion of the Background

As an important intermediate for the synthesis of pharmacologically active compounds, in particular of antiviral active compounds, the nucleic acid base guanine is of great importance. Guanine is needed, for example, as a precursor for acyclovir, which according to DE-A-35 44 461, incorporated herein by reference, is suitable for the therapy of viral infections.

The reaction of 4,5-diaminopyrimidine sulfates with formamide to give the corresponding purines is well-known (Robins et al., J. Am. Chem. Soc. 75 (1953) 263). 2,4,5-Triamino-6-hydroxypyrimidine sulfate (TAHP sulfate) is employed for the synthesis of guanine. According to DE-A-37 29 471, guanine can be obtained by heating a suspension of TAHP sulfate in formamide to up to 200° C. with removal by distillation of the water of reaction formed. A disadvantage in this process is that formamide partially decomposes at the high temperatures needed, which in addition to the formation of carbon monoxide and ammonia, results in colored guanine crude products which necessitate a high expenditure on purification. The necessity to employ the TAHP, which is unstable in free form, in the form of its sulfate causes a high salt load, which is a further disadvantage.

According to EP-A-0 415 028, guanine is obtained by reaction of TAHP sulfate with alkali metal formate and formic acid. Although this process avoids the disadvantages associated with the use of formamide, it also leads, however, to production of an economically and ecologically unfavorable high unavoidable salt load in the form of alkali metal sulfate in the reaction mixture.

In the process based on TAHP sulfate described above, 2,4-diamino-5-formylamino- 6-hydroxypyrimidine (referred to as DAFHP below) is passed through as an intermediate, which is reacted in situ to produce guanine.

According to DE-A-41 36 114, guanine can also be obtained starting from isolated DAFHP by heating in formamide to at least 140° C. The ratio of DAFHP to formamide is 1:2 to 1:3. Up to 10% of formic acid can be added to the reaction mixture. The DAFHP employed here is obtained, for example, by a process according to EP-A-0-267 594, in which 2,4-diamino-6-hydroxy-5-nitrosopyrimidine is catalytically hydrogenated and reacted to give TAHP sulfate. After the hydrogenation, the reaction mixture is treated with formic acid, if appropriate with addition of a mineral acid, in order to obtain DAFHP quantitatively. Although the process described in DE-A-41 36 114 is salt-free, it has, however, the already mentioned disadvantages which accompany the use of formamide (such as decomposition, and expensive purification of the final product). The guanine according to DE-A-41 36 114 is obtained with a purity (HPLC) of less than 98.0%. After purification, losses in yield therefore occur.

Accordingly, there remains a need for a process for producing guanine which overcomes the disadvantages discussed above.

SUMMARY OF THE INVENTION

It is an object of the present invention to provide a process for producing guanine.

It is also an object of the present invention to provide a process for producing guanine which does not have the mentioned disadvantages the known processes described above, and in which guanine may be obtained in high space-time yield and purity.

The objects of the invention, and others, may be accomplished with a process for the preparation of guanine starting from 2,4-diamino-5-formylamino-6-hydroxypyrimidine (DAFHP), which comprises reacting isolated DAFHP in the absence of formamide in formic acid, with or without addition of water under reflux conditions, to produce guanine.

A more complete appreciation of the invention and many of the attendant advantages thereof will be readily obtained as the same becomes better understood by reference to the following detailed description.

DETAILED DESCRIPTION OF THE INVENTION

The starting material for the inventive process may be isolated DAFHP. Isolated DAFHP may be obtained, for example, by the process described in EP-A-0267594, incorporated herein by reference.

Based on DAFHP, preferably up to 2 equivalents, particularly preferably 0.5 to 1.5 equivalents, of water may be added during the reaction. The use of more than 2 equivalents of water causes an increased expenditure on purification of the resulting guanine and is therefore not preferred. The reaction may be carried out at normal pressure and at a temperature which is established when water containing formic acid boils under reflux.

It has surprisingly and unforeseeably been shown that the inventive process permits the use of high molar DAFHP concentrations, which is a particular advantage of the present invention. In the embodiment without addition of water, the molality (based on DAFHP) is up to 2.5, preferably 1.80 to 2.25. The reaction time is 12 to 24 hours, preferably 15 to 18 hours. Longer reaction times are possible in principle, but lead to no significant improvement; moreover longer reaction times contradict the aim according to the invention of a high space-time yield. Shorter reaction times result in marked losses in yield due to unreacted DAFHP. However, it has turned out to be particularly surprising that the preferred embodiment with addition of water not only allows a second marked increase in the molar DAFHP concentration, but moreover also a marked reduction in the reaction time. The molality in this embodiment is up to 5.0, preferably 3.2 to 4.2. The reaction time is 9 to 15 hours, preferably 10 to 12 hours. More than a four-fold space-time yield is achieved here in comparison with EP-A-0415028 (0.9 molal based on TAHP sulfate).

In the process according to the invention, after the reaction is complete formic acid and water may be removed by distillation, which is preferably carried out under reduced pressure. The water-containing formic acid thus recovered is very pure and can be employed in other processes. In particular, the recovered water-containing formic acid can be used in the preparation of the starting substance DAFHP, which is a further advantage of the present invention.

The guanine obtained may be purified using well-known methods. For example, the crude product can be dissolved in aqueous alkali metal hydroxide and treated with active carbon. Guanine may then be isolated by precipitation, preferably by precipitation by hydrolysis, as described in DE-A-37 23 874, incorporated herein by reference. The process according to the invention provides guanine in very good yields of, for example, 98% of theory as a crude product. After purification, guanine can be obtained in good yields of customarily 92% of theory and more as a final product. The pure guanine obtained by this process has a purity (HPLC) of more than 99.5%.

The guanine prepared by the process according to the invention can be used as an intermediate for the synthesis of pharmacologically active compounds. In a particularly preferred embodiment, the pharmacologically active compound is an anti-viral agent. A preferred anti-viral agent is acyclovir. Acyclovir may be obtained from the guanine produced by the present process as described in, for example, DE-A-35 44 461, incorporated herein by reference.

Having generally described this invention, a further understanding can be obtained by reference to certain specific examples which are provided herein for purposes of illustration only and are not intended to be limiting unless otherwise specified.

EXAMPLES

Example 1

67.6 g (0.4 mol) of DAFHP are introduced into 222.2 g of formic acid (98–100% strength) in portions with stirring (the molality is 1.8 based on DAFHP)The mixture is heated to boiling, and the readily stirrable suspension is then kept under reflux for 18 hours. Formic acid and water are then almost completely removed by distillation in a water-jet vacuum. The crude guanine obtained is purified in a known manner by dissolving it in aqueous alkali metal hydroxide, treating with active carbon (15% by weight) and subsequent precipitation by hydrolysis. Starting from 10 g of crude product (aliquot part), after a single use of this purification process 9.61 g (95.9% of theory) of guanine having a purity (HPLC) of 99.8% are thus obtained.

Example 2

First 7.2 g (0.4 mol) of water and then 67.6 g (0.4 mol) of DAFHP are added t-o 111.1 g of formic acid (98–100% strength) in portions with stirring (the molality is 3.4 based on DAFHP). The mixture is heated to boiling, and the readily stirrable suspension is then kept under reflux for 12 hours. Formic acid and water are then almost completely removed by distillation in a waterjet vacuum. Purification is carried analogously to Example 1. Guanine having a purity (HPLC) of 99.9% is thus obtained in a yield of 91.8% of theory.

Comparative Example
(According to EP-A-0415028)

The TAHP sulfate concentration in the reaction mixture is twice as high in this comparison example as in EP-A-0 415 028.

A mixture of 111.1 g of formic acid (98–100% strength), 47.8 g (0.2 mol) of TAHP sulfate and 28.6 g (0.42 mol) of sodium formate is heated to boiling.

After reaching the reflux temperature, the reaction mixture becomes unstirrable. The stirrability improves gradually in the course of several hours. Only after approximately 5 hours is a stirrable suspension present. The reaction mixture is kept under reflux for a total of 18 hours. The crude product obtained after distillation of water and formic acid in a water-jet vacuum contains, in addition to 84.2% of guanine, 14.3% of the unreacted intermediate DAFHP according to HPLC.

Obviously, numerous modifications and variations of the present invention are possible in light of the above teachings. It is therefore to be understood that within the scope of the appended claims, the invention may be practiced otherwise than as specifically described herein.

This Application is based on German Patent Application Serial No. 198 39013.0, filed on Aug. 27, 1998, and incorporated herein by reference.

What is claimed is:

1. A process for preparing guanine, comprising:
   reacting 2,4-diamino-5-formylamino-6-hydroxypyrimidine (DAFHP) in formic acid to which 0.5 to 2 equivalents of water is added relative to the (DAFHP) reactant under reflux conditions for 12 to 24 hours, in the absence of formamide, to produce guanine.

2. The process of claim 1, wherein the reaction time is 15 to 18 hours.

3. The process of claim 1, wherein the reaction is carried out at normal pressure and at a temperature which is established when water-containing formic acid boils under reflux.

4. The process of claim 1, wherein the molal concentration of the DAFHP in the reaction mixture is up to 2.5.

5. The process of claim 1, wherein the molal concentration of the DAFHP in the reaction mixture is 1.80 to 2.25.

6. The process of claim 1, further comprising isolating the guanine.

7. The process of claim 1, wherein after the reaction is complete formic acid and water are removed by distillation under reduced pressure and the guanine obtained is purified in an aqueous alkaline solution over active carbon, and, after subsequent precipitation, is isolated by precipitation by hydrolysis.

8. A process for preparing guanine, comprising reacting 2,4-diamino-5-formylamino-6-hydroxypyrimidine (DAFHP) in formic acid to which water is not added during the reaction under reflux conditions for 9 to 15 hours, in the absence of formamide, to produce guanine.

9. The process of claim 8, wherein the reaction time is 10 to 12 hours.

10. The process of claim 8, wherein the molal concentration of the DAFHP in the reaction mixture is up to 5.0.

11. The process of claim 8, wherein the molal concentration of the DAFHP in the reaction mixture is 3.2 to 4.2.

12. The process of claim 8, wherein the reaction is conducted at normal pressure and at a temperature which is established when water-containing formic acid boils under reflux.

13. The process of claim 8, further comprising isolating the guanine.

14. The process of claim 8, wherein after the reaction is complete formic acid and water are removed by distillation under reduced pressure and the guanine obtained is purified in an aqueous alkaline solution over active carbon, and, after subsequent precipitation, is isolated by precipitation by hydrolysis.

15. A process for preparing guanine, comprising:
    reacting 2,4-di amino-5-formylamino-6-hydroxypyrimidine (DAFHP) in a molal concentration of 1.80 to 2.25 in formic acid reaction medium under reflux conditions, in the absence of formamide, to produce guanine.

16. The process of claim 15, wherein the reaction is conducted at normal pressure and at a temperature which is established when water-containing formic acid boils under reflux.

17. The process of claim 15, further comprising isolating the guanine.

18. The process of claim 15, wherein after the reaction is complete formic acid and water are removed by distillation under reduced pressure and the guanine obtained is purified in an aqueous alkaline solution over active carbon, and, after subsequent precipitation, is isolated by precipitation by hydrolysis.

* * * * *